United States Patent [19]

Yamaji et al.

[11] Patent Number: 4,458,067

[45] Date of Patent: Jul. 3, 1984

[54] PROCESS FOR PRODUCING $N^6,O^{2'}$-DIACYLADENOSINE-3',5'-CYCLIC PHOSPHORIC ESTER ALKALI METAL SALTS

[75] Inventors: Nobuyuki Yamaji, Noda; Kyoko Tahara, Kashiwa; Motohiko Kato, Noda, all of Japan

[73] Assignee: Kikkoman Corporation, Noda, Japan

[21] Appl. No.: 336,612

[22] Filed: Dec. 30, 1981

[30] Foreign Application Priority Data

Jul. 7, 1980 [JP] Japan ................... 55-91702

[51] Int. Cl.³ .................. C07H 15/12; C07H 17/00
[52] U.S. Cl. ............................................. 536/27
[58] Field of Search ...................................... 536/27

[56] References Cited

U.S. PATENT DOCUMENTS 3,810,883  5/1974  Smith ................... 536/27
3,849,397  11/1974  Robins et al. ........... 536/27
4,058,659  11/1977  Robins et al. ........... 536/27

FOREIGN PATENT DOCUMENTS 48-16119  7/1973  Japan.
52-39698  3/1977  Japan.

OTHER PUBLICATIONS

Falbriard et al., (1967), Biochim. Biophys. Acta, vol. 148, pp. 99–105.

Primary Examiner—Ethel G. Love
Attorney, Agent, or Firm—Banner, Birch, McKie & Beckett

[57] ABSTRACT

An $N^6,O^{2'}$-diacyladenosine-3',5'-cyclic phosphoric ester alkali metal salt can be obtained with ease and in a high yield by reacting an adenosine-3',5'-cyclic phosphoric ester alkali metal salt with a carboxylic anhydride having 4 or less carbon atoms at a temperature of 70° C. or above.

5 Claims, 1 Drawing Figure

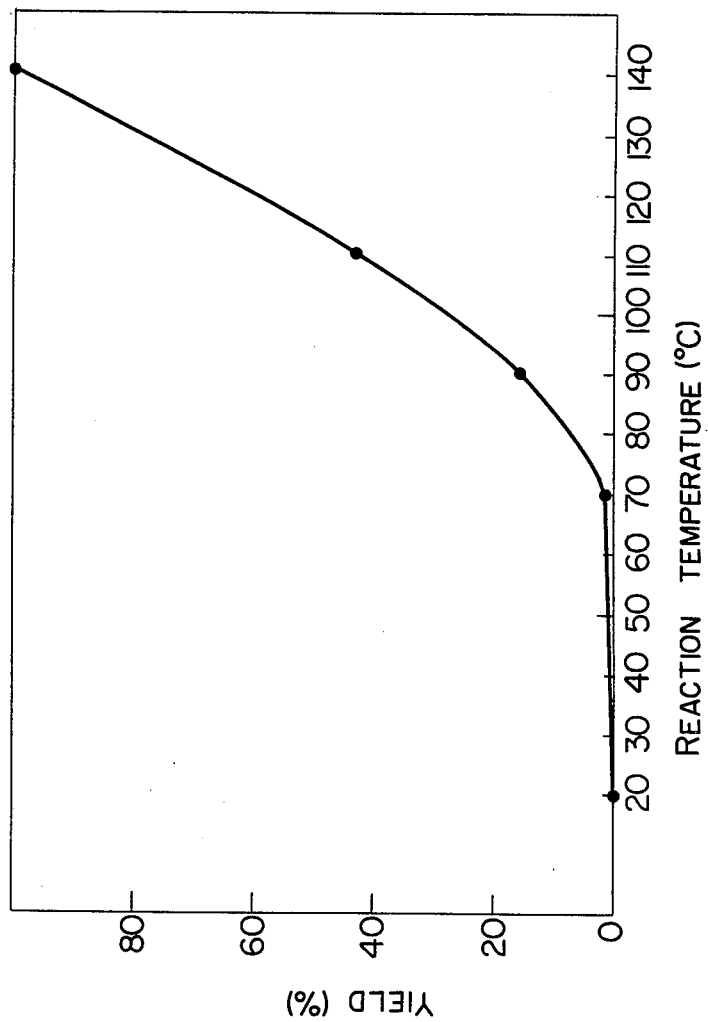

PROCESS FOR PRODUCING N⁶,O²'-DIACYLADENOSINE-3',5'-CYCLIC PHOSPHORIC ESTER ALKALI METAL SALTS

This invention relates to a process for producing $N^6,O^{2'}$-diacyladenosine-3',5'-cyclic phosphoric ester alkali metal salts.

$N^6,O^{2'}$-Diacyladenosine-3',5'-cyclic phosphoric ester alkali metal salts (hereinafter referred to as diacyl-C-AMP alkali metal salts), particularly sodium salts, are useful as a reagent in pharmaceutical and biochemical researches.

It is reported that diacyl-C-AMP sodium salts act on the sarcoma cells formed from a test tube reaction with, for example, 3-methylcholanthrene, a known carcinogenic substance, and the RSV-induced rat sarcoma cells to change such morbid cells into one which can hardly be distinguished from the normal cells even under a morphological observation with a microscope (see Proceedings of the National Academy of Science, Vol. 68, p. 425, 1971).

Various methods are known for the production of diacyl-C-AMP alkali metal salts, particularly diacyl-C-AMP sodium salts. For example, di-n-butyryl-C-AMP sodium salt can be obtained by reacting a C-AMP triethylamine salt with an n-butyric anhydride in a solvent such as pyridine, adding water to the reaction mixture, allowing it to stand at 4° C. for 5 hours to decompose excess n-butyric anhydride into n-butyric acid, separating it by extraction with ether, and further treating the residual solution with a sodium type cation exchange resin to convert the triethylamine salt into a sodium salt (see Japanese Patent Publication No. 16119/77). In another known method (Japanese Patent Application Kokai (Laid-Open) No. 39698/77), C-AMP or a tertiary amine salt thereof is used as starting material, and a tertiary amine such as triethylamine, pyridine, etc., or a combination of such tertiary amine and an organic solvent such as a hydrocarbon halide, an aliphatic ketone, an aliphatic nitrile or an ether is used as the solvent and/or acid bonding agent.

Any of these known methods, however, is complicated in the preparation process and also economically disadvantageous because of high cost of the solvent and/or acid bonding agent used, particularly pyridine or the like. Further, a salt exchange is required for converting the obtained diacyl-C-AMP tertiary amine salt into a useful sodium salt.

The present inventors have made more extensive studies for eliminating these defects of the conventional methods and found as a result that $N^6,O^{2'}$-diacyladenosine-3',5'-cyclic phosphoric ester alkali metal salts represented by the general formula (I):

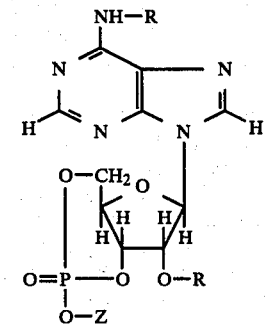

(wherein Z is an alkali metal atom, and R is an acyl group), can be obtained advantageously by reacting adenosine-3',5'-cyclic phosphoric ester alkali metal salts represented by the general formula (II):

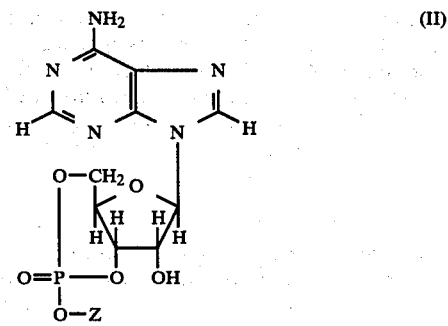

(wherein Z is an alkali metal atom), with an anhydride of a carboxylic acid having 4 or less carbon atoms at a temperature of 70° C. or above.

An object of this invention is to provide the improved $N^6, O^{2'}$-diacyladenosine-3'5'-cyclic phosphoric ester alkali metal salts.

Other objects and advantages of this invention will become apparent from the following detailed descriptions.

According to the process of this invention, the objective substance of the formula (I) can be obtained in a high yield by more simple and economical means than the prior methods. The process of this invention can dispense with salt exchange required in the conventional methods, thus allowing simplification of the preparation process. It also makes unnecessary the use of an expensive solvent to greatly facilitate the refining operation. Thus, the process of this invention is best suited for the applications on an industrial scale.

The accompanying drawing is a graph showing the relation between the reaction temperature and the yield of di-n-butyryl-C-AMP sodium salt, which relation is to be discussed later.

The starting material of the formula (II) may be obtained, for example, by neutralizing the phosphoric acid moiety of an adenosine-3',5'-cyclic phosphoric ester (C-AMP) in a usual way, for example, by using a hydroxide of an alkali metal. Sodium salt, potassium salt and the like may be cited as the alkali metal salt used in this invention, but sodium salt is most preferred.

As the carboxylic anhydride having 4 or less carbon atoms, there may be used, for example, acetic anhydride, propionic anhydride and butyric anhydride. Among them, butyric anhydride is preferred.

The process of this invention may be practiced, for example, in the following way. A C-AMP alkali metal salt (II) is reacted with a carboxylic anhydride having 4 or less carbon atoms at a temperature above 70° C., preferably from 110° C. to 200° C. The reaction time is usually from several hours to several days. The carboxylic anhydride is used usually in an amount more than thrice the molar quantity, preferably 4 to 50 times the molar quantity of the C-AMP alkali metal salt (II).

The reaction is preferably carried out by using an excess amount of a carboxylic anhydride, but if desired, it may be conducted in the presence of a polar solvent such as water, a carboxylic acid, etc., or a mixture thereof, in which case the reaction time can be shortened.

The separation and purification of the objective compound can be accomplished in a usual way. For example, the reaction mixture is distilled under reduced pressure, or first the excess reagent is extracted and separated by using an organic solvent such as ether and then the residue is crystallized by a usual means or subjected to column chromatography using silica gel, alumina or the like to obtain the pure objective compound (I).

The present invention will be illustrated in more detail with reference to the following examples, but the present invention is not limited thereto.

Experimental Example

The following experiment was carried out to determine the optimal reaction temperature.

200 mg Of C-AMP sodium salt was suspended in 4.0 ml of n-butyric anhydride and they were reacted under stirring at various temperatures for 40 hours. After completion of the reaction, 5 μl of the reaction mixture was spotted on a filter paper (Toyo filter paper No. 51A) and developed for 16 hours by using a 0.5M ammonium acetate/ethanol (2:5 by volume) mixed solvent. Then the portion containing the di-n-butyryl-C-AMP sodium salt was cut out and extracted with methanol, and the absorbance of the methanol layer at the wavelength of 272 mμ was measured.

The thus obtained values of absorbance were applied to the standard calibration curve (formulated from the methanol solutions of di-n-butyryl-C-AMP sodium salt of various known concentrations and their absorbances) to determine the amount of the objective compound produced, and the yield was calculated therefrom. The change in yield of the di-n-butyryl-C-AMP sodium salt depending on the reaction temperature is graphically shown in the accompanying drawing.

When the reaction was carried out at room temperature (20° C.), there was produced little objective compound, but as seen from the graph, when the reaction temperature was above 70° C., the yield increased sharply with rise of the temperature. The yield was about 50% at the reaction temperature of 110° C., and it reached about 100% at 140° C. The upper limit of the reaction temperature is preferably set at about 200° C. in consideration of the relation with the boiling point of the carboxylic anhydrides.

EXAMPLE 1

2.0 ml Of n-butyric anhydride was added to 400 mg of C-AMP sodium salt and reacted under stirring at 140° C. for 16 hours. The reaction mixture was filtered and the filtrate was added with 15 ml of diethyl ether, and the isolated precipitate was filtered out. The resulting crude crystals were washed with diethyl ether and recrystallized from aqueous acetone, whereby 450 mg of dibutyryl-C-AMP sodium salt was obtained. This corresponds to a yield of 80% by molar ratio based on the starting material.

The thus obtained dibutyryl-C-AMP sodium salt had the following physicochemical properties.

| DEAE cellulose thin-layer chromatography | |
| --- | --- |
| Developing solvent: | ethanol/0.5M ammonium acetate (7:2 by volume) |
| Rf: | 0.57 |
| Detection method: | pen ray quartz lamp (short wave UV) |
| Untraviolet absorption spectrum: | $\lambda_{max}^{C_2H_5OH} = 272$ mμ |
| IR absorption spectrum: | 1740, 1920, 1610, 1460, 1245 cm$^{-1}$ |
| Melting point (measured by a microquantity melting point apparatus): | 203°–205° C. |

EXAMPLE 2

A 1N sodium hydroxide solution was added to 1.0 g of C-AMP till it was neutralized, and the solution was evaporated to dryness and further dried.

The resulting C-AMP sodium salt was added with 45 ml of n-butyric anhydride and 5 ml of n-butyric acid and mixed sufficiently, and the mixture was reacted under stirring at 120° C. for 16 hours. Then the reaction mixture was added with 500 ml of diethyl ether and extracted thrice with 10 ml portions of water, and the water layers were combined and concentrated under reduced pressure. The residue was added with ethanol and then with diethyl ether successively to obtain 1.15 g of di-n-butyryl-C-AMP sodium salt. This corresponds to a yield of 77% by molar ratio based on the starting material. The thus obtained di-n-butyryl-C-AMP sodium salt had the same physicochemical properties as those of the compound obtained in Example 1.

What is claimed is:

1. A process for producing an $N^6,O^2$-diacyladenosine-3',5'-cyclic phosphoric ester alkali metal salt represented by the general formula:

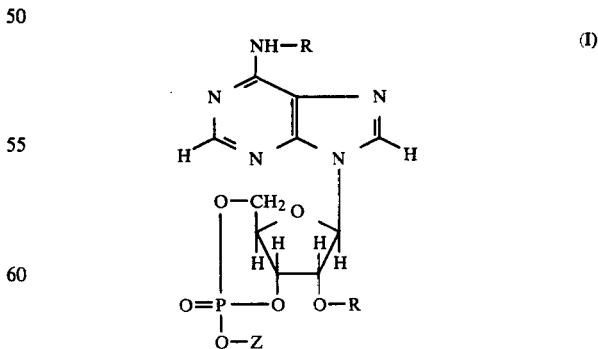

wherein Z is an alkali metal atom, and R is an acyl group, which comprises reacting an adenosine-3',5'-cyclic phosphoric ester alkali metal salt represented by the general formula:

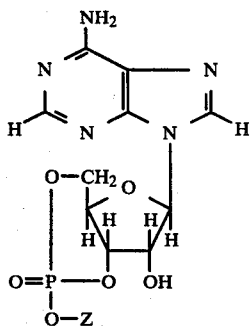 (II)

wherein Z is an alkali metal atom, with a carboxylic anhydride having 4 or less carbon atoms in the absence of solvent and at a temperature in the range of from 70° C. to about 200° C., said carboxylic anhydride in an amount which is at least a thrice molar quantity of the adenosine-3',5'-cyclic phosphoric ester alkali metal salt (II).

2. The process according to claim 1, wherein the alkali metal salt is sodium salt or potassium salt.

3. The process according to claim 1, wherein the carboxylic anhydride having 4 or less carbon atoms is acetic anhydride, propionic anhydride or butyric anhydride.

4. The process according to claim 1, wherein the reaction temperature is from 110° to 200° C.

5. The process according to claim 1, wherein the amount of the carboxylic anhydride added is 4 to 50 times the molar quantity of the adenosine-3',5'-cyclic phosphoric ester alkali metal salt (II).

* * * * *